United States Patent [19]

Stolle et al.

[11] Patent Number: 4,762,712
[45] Date of Patent: Aug. 9, 1988

[54] ANTI-MASTITIS POLYVALENT VACCINE, METHOD OF ADMINISTRATION AND METHOD FOR PRODUCTION THEREOF

[75] Inventors: Ralph J. Stolle, Oregonia, Ohio; Lee R. Beck, Birmingham, Ala.

[73] Assignee: Stolle Research & Development Corporation, Cincinnati, Ohio

[21] Appl. No.: 528,132

[22] Filed: Aug. 31, 1983

[51] Int. Cl.$^4$ .......................... A61K 39/02; C12N 1/20
[52] U.S. Cl. ......................................... 424/92; 435/253
[58] Field of Search ........................ 435/68, 253, 243; 424/92

[56] References Cited

U.S. PATENT DOCUMENTS

| | | | |
|---|---|---|---|
| 3,917,818 | 11/1975 | Botes | 424/87 |
| 4,197,290 | 4/1980 | Yoshida | 424/92 |
| 4,327,082 | 4/1982 | Armitage | 424/88 |
| 4,425,330 | 1/1984 | Norcross et al. | 424/92 |

Primary Examiner—Blondel Hazel
Attorney, Agent, or Firm—Oblon, Fisher, Spivak, McClelland & Maier

[57] ABSTRACT

A process for the production of a polyvalent vaccine effective in the prevention and treatment of mastitis in bovine animals is disclosed, which comprises periodically culturing the milk of animals exhibiting preclinical mastitis to cultivate any pathogens present therein, killing those pathogens and incorporating each strain of cultivated, killed pathogen in a pharmacological carrier together with all other strains previously identified. The process is repeated to ensure all newly appearing pathogenic strains are vaccinated against. The vaccine so produced has been demonstated to be effective in reversal of hard udder syndrome.

4 Claims, 1 Drawing Sheet

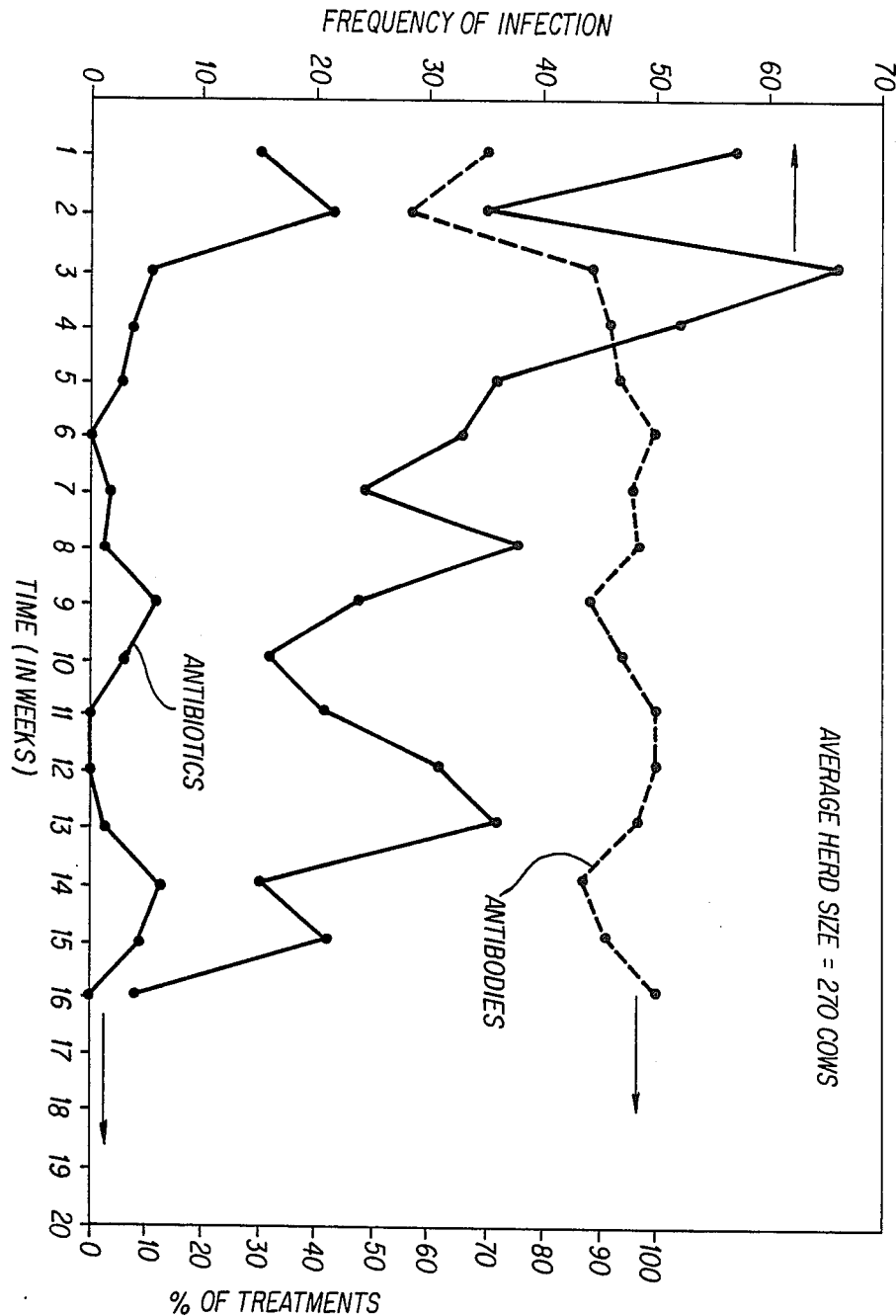

ANTI-MASTITIS POLYVALENT VACCINE, METHOD OF ADMINISTRATION AND METHOD FOR PRODUCTION THEREOF

BACKGROUND OF THE INVENTION

1. Field of the Invention

This invention relates to a polyvalent vaccine or medication for the treatment and prevention of mastitis in bovine animals, and a method of producing that vaccine. Specifically, this invention is directed to a process for preparing a therapeutic and prophylactic vaccine of broad applicability, and the vaccine produced thereby.

2. Description of the Prior Art

Infection of the mammary gland in bovine animals, particularly dairy cattle, which is commonly referred to as mastitis, represents a major health problem to the dairy industry. Mastitis causes a loss of milk production by infected cows, and it is estimated that the average dairy farmer loses approximately $400/cow per year due to mastitis. This represents an overall financial loss of about $26,000 per year for a dairy herd consisting of 200 milking cows. On a national scale, this loss is staggering.

Conventionally, methods and products for the prevention and treatment of mastitis include the use of sanitary milking techniques and chemical antibiotics, which are either perfused into the infected udder through the tit canal or injected into the muscle of the animal. However, the antibiotics which are used to treat mastitis cannot be employed to prevent the occurrence of mastitis because antibiotic derivatives which appear in the milk following treatment are not safe for human consumption. As a result, antibiotic contaminated milk must be discarded, and this represents a further financial loss to farmers. Although, in some situations, antibiotic contaminated milk may be fed to calves, this practice poses the severe hazard of harming the calves. Accordingly, conventional methods remain unsatisfactory to prevent the occurrence of mastitis, and represent a large financial loss when used to treat mastitis.

Further, chronic infection of the cow udder causes the milk-producing tissues to feel hard to the touch when the udder is palpated. This condition in dairy cattle is commonly referred to as "hard udder". Under conventional practices, once the udder hardens, milk production is reduced and remains compromised even after the infection ceases. There is no known method or product in the prior art that will reverse the hard udder condition once it occurs, and this condition generally presists for the life of the cow.

Recently, attempts have been made to develop vaccines for immunization against mastitis. However, these have for the most part been unsuccessful, particularly due to the wide spectrum of different pathogens that can cause mastitis. A number of polyvalent vaccines, which include different combinations of bacterial strains and other pathogens known to cause mastitis have been developed and tested. However, none of these have proved to be highly effective in preventing the disease over an extended period of time. Further, they have not been successful in treating mastitis and reversing hard udder syndrome. In spite of the great financial impact mastitis has on the dairy industry, there has been little or no progress in the prevention and/or treatment of mastitis.

Accordingly, an industry-wide need persists for a vaccine for the treatment and prevention of mastitis in bovine animals over an extended period of time, and a method of reversing hard udder syndrome.

SUMMARY OF THE INVENTION

It is one object of this invention to provide a method whereby a vaccine may be developed for the prevention of mastitis in bovine animals.

It is another object of the invention to provide a method whereby a vaccine is produced which is effective in treating mastitis in bovine animals, without compromising the quality of the milk of the animal.

It is yet another object of this invention to provide a process for developing a vaccine, and the vaccine, which is capable of preventing mastitis over a long period of time.

It is yet a further object of this invention to provide a vaccine which can be employed to reverse hard udder syndrome.

These and other objects may be achieved by practice of the invention described and claimed hereinbelow.

A polyvalent vaccine may be produced which has been demonstrated to be effective in the prevention and treatment of mastitis in bovine animals over an extended period of time. Further, the same vaccine has been demonstrated to be effective in reversing hard udder syndrome.

The vaccine is produced by a process which comprises periodic sampling of the milk of all the members of a bovine animal herd or herds for diagnosis of preclinical mastitis. The milk samples of those animals so diagnosed are cultured, to cultivate pure strains of each of the pathogens present in the milk. Thereafter, those pathogens are killed and incorporated in an appropriate pharmacological carrier in a concentration suitable for the prevention and treatment of mastitis. The periodic sampling is repeated on an average of about once every month, and any pathogen strain that is cultivated that was not previously incorporated in the vaccine is killed and so incorporated. Accordingly, the composition of the vaccine changes over time, incorporating new pathogens as they appear in the herd animals exhibiting preclinical mastitis. Over time, a sufficiently broad spectrum vaccine is provided such that it may be used with animals not members of the herds originally employed in creating the vaccine.

A vaccine prepared according to this process has been demonstrated to be effective in the prevention and treatment of mastitis in bovine animals. Further, and even more surprisingly, this vaccine has been demonstrated to be effective in reversing hard udder syndrome, and restoring milk production capacity to affected animals.

This invention may be better understood by reference to the detailed description provided below.

BRIEF DESCRIPTION OF THE DRAWINGS

FIG. 1 is a graphic illustration of the relationship of the frequency of mastitis infections observed during simultaneous and varying treatment with the vaccine of this invention and antibiotics.

DETAILED DESCRIPTION OF THE PREFERRED EMBODIMENTS

The vaccine of this invention, and the process for making it, are suitable for bovine animals. Preferably, these animals include sheep, cows and goats. Cows are particularly preferred as animals responsive to the vaccine of this invention. Although the process and vaccine may be applied to any bovine animals, they will be described with reference below to cows, for purposes of clarity.

The discovery of the process for making the vaccine of this invention rests on the knowledge that many different kinds of generic species of pathogens (microorganisms generally including bacteria, although virus and other infection vectors may be involved) can cause infection in the mammary glands of cattle. These infections are collectively referred to as mastitis. Therefore, mastitis per se can be caused by many different kinds of pathogens. Although some of the pathogen species are known and can be identified by those of skill in the art, many strains remain unknown, and unidentified.

It is impossible to list the full spectrum of microorganisms that are capable of causing mastitis. Treatment and prevention of mastitis is further complicated by the fact that it is often due to mixed infections of the mammary glands, such that pathogens of both known and unknown identity may simultaneously infect the mammary gland of the cow, each contributing to the overall clinical condition referred to as mastitis. This is the reason why treatment against one specific type of pathogen or group of pathogens is not totally effective in preventing mastitis, and may have little impact in therapeutic treatment.

It has been discovered that generally, individual dairy herds harbor a unique combination of pathogens which are capable of causing mastitis. Further, it has also been found that the pathogenic population within a given herd or herds is continually changing as new species come and go. The change in the population occurs by various processes. For example, evolutionary change may produce new strains of pathogens capable of causing mastitis; the introduction of new cattle in the herd introduces new strains of pathogens as well; some strains may be eliminated by natural immunity; changes in weather and/or other environmental conditions may selectively favor the growth and development of certain strains of bacteria; further, the method of handling the cattle and/or changes in personnel handling the cattle may affect the kinds of pathogenic strains to which the cattle are exposed. Indeed, the use of chemical antibiotics such as penicillin, tetracycline, etc., may promote the evolution of new strains which are resistant to the very antibiotics being used.

In light of the above, it is apparent that an effective method for the prevention and treatment of mastitis over time must keep pace with the changing pathogens that cause the disease. Moreover, since dairy herds in general harbor slightly differing populations of pathogens, a truly selective method of treatment, based on conditions in one herd, may not be suitable for use in other herds unless it is of sufficiently broad spectrum to ensure coverage against most commonly encountered pathogens. Therefore, the treatment must be amenable to change as the strains of pathogens change or evolve. Anything less than this may result in temporary benefits, but in the long run would have no significant impact on the incidence or treatment of mastitis within a given dairy herd.

The method of treatment of this invention involves immunization of the dairy cow with pathogen strains which cause mastitis using a mixed vaccine which may be custom-tailored to the individual dairy herd or therapeutic treatment with the same vaccine. Moreover, the process for producing the vaccine, and the vaccine itself, is dynamic. That is, the species comprising the vaccine may be continually altered to accommodate changes in the pathogen species which occur in a dairy herd. Since the composition of the vaccine is changing, over time and between herds, it is not possible to characterize the product of the invention by listing the bacterial species that comprise the vaccine, save for any unique point in time and unique herd.

Starting with a small number of dairy herds, a broad spectrum vaccine generally effective in the prevention and treatment of mastitis may be prepared according to the process of this invention. Milk from individual cows is collected and examined histologically for the presence of white blood cells. If the white blood cell count in a milk sample is above the established norm for the individual, that cow is diagnosed as having preclinical mastitis. Similarly, pathological evidence of infection by viral or other types of pathogens capable of causing mastitis can be observed.

The milk samples from cows exhibiting preclinical mastitis is collected, and pathogen cultures (principally bacterial) are cultivated, using different culture media and growing conditions, as shown in Table 1. For the purposes of clarity, this process is further described with respect to bacterial pathogens. However, those of skill in the art will be aware that some or related processes can be used for other pathogens.

TABLE 1

List of Growth Media

| Growth Media | pH |
|---|---|
| A.C. Broth | 7.4 |
| Actinomyces Broth | 6.9 |
| APT Broth | 6.7 |
| Bacto-Penassay Broth | 7.0 |
| Brain Heart Infusion Broth | 7.4 |
| Mycophil Broth | 7.0 |
| Nutrient Broth | 6.8 |
| Trypticase Soy Broth | 7.3 |
| Thioglycollate Medium | 7.0 |
| Tryptose Phosphate Broth | 7.3 |

The species obtained from these cultures are then grown in bulk quantity of pure strains. This may be achieved by swabbing the sample over Trypticase Soy Agar (TSA). Antibiotic sensidiscs including novobiocin, chlortetracycline, streptomycin, ampicillin, chloramphenicol, penicillin, oxytetracycline, erythromycin and cephalothin are applied, and the plate is incubated overnight, generally at about 37° C.

Antibiotic-resistant pathogens are isolated by looping a small amount of growth off the agar plate and streaking it over fresh TSA plates to obtain individual colonies. The colonies are compared for similarity of size, shape, color, translucence, etc. If more than one bacteria is observed, the streaking/incubating/analyzing procedure is repeated until pure strains of bacteria are isolated.

Once purity of the bacterial culture is confirmed, the colonies are looped into tubes containing brain heart infusion and APT broth, to determine which media is more advantageous to bacterial growth. Other media known to those of skill in the art may be employed. The tubes are again incubated overnight, or until substantial growth is observed.

One half of the suspension so obtained is sterilized and maintained at low temperatures, for reference material. The other half is used to inoculate one liter of the preferred growth media, which is again incubated until substantial growth is observed. The bacteria are harvested by centrifuging the suspension for twenty minutes to remove the media. The derived pellet is resuspended in saline solution and centrifuged three different times to ensure complete washing of the bacteria. After the third spin, the pellet is resuspended in a small amount of distilled water.

The isolated bacteria must be then converted to a non-virulent form in order to be used as a vaccine. The vaccine can be prepared according to a number of well-known methods in the art. Thus, the vaccine can be prepared from the whole bacteria after heat killing, or from immunologically active but non-pathogenic subcomponets thereof, as is commonly practiced in the art. Chemically attenuated live or killed bacterial vaccines can also be prepared, for example by the treatment of the bacteria with chemical agents decreasing pathogenicity while allowing the bacteria to retain immunogenicity. Other techniques are similarly known in the art to attenuate the virulence of the bacterial strain or strains employed. One technique is to employ developed avirulent or slow growing strains, or mutants incapable of sustained replication in the host. This is generally known in the art as genetic attenuation and can be done by genetic manipulation or by serial passages. Although a large number of methods of securing non-virulent forms of the bacteria and other pathogens isolated will occur to those of skill in the art, among preferred non virulent forms are genetically attenuated bacterial, chemically attenuated bacteria, immunogenetically active portions of the bacteria, such as cell walls, synthetic protein portions of the bacteria, killed bacteria and mixtures thereof.

In a particularly preferred embodiment, the bacteria are heat-killed by heating the media-free bacteria suspension in a glass flask at 80° C., overnight, or higher temperatures, if necessary. The viability of the bacteria so killed is determined by inoculating broth with a small amount of the heat killed bacteria. The broth is again incubated and checked daily for growth. The pathogen must be killed for use in the vaccine. The killed bacteria are lyophilized until dry.

Non-virulent bacteria samples are mixed with a sterile saline solution, or similar acceptable pharmacological carrier, in a biologically effective concentration. Although effective concentrations will vary from herd to herd and pathogen to pathogen, and may be determined by those of ordinary skill in the art without the exercise of inventive faculty, it has been established that a concentration of $2 \times 10^{10}$ total pathogenic cells per milliliter of saline is a generally effective concentration for bacterial pathogens.

All members of the herds are immunized, using the vaccine produced by the process described above, by injecting the vaccine into the leg muscle. A preferred dose of vaccine is 15 milliliters given every two weeks.

Milk from all of the cows in the immunized herd(s) is examined every 30 days, or other effective period that may be established, for the presence of preclinical mastitis. If preclinical mastitis is detected, the above procedures are repeated, and any new bacterial strains obtained from the infected cows are added to the existing vaccine.

As will be apparent, by following the process of this invention, each time a new pathogenic strain appears which causes preclinical mastitis, it is detected, collected, grown in culture, and added to the vaccine. Accordingly, the formulation of the vaccine is subject to continuous additions. This is a dynamic process which results in the evolution of a complex and unique vaccine, the composition of which will vary between herds.

Over a short period of time, depending on the number of herds employed, a broad spectrum vaccine effective in the treatment and prevention of mastitis induced by most common pathogens is prepared by the above process. This "base" vaccine may be administered to animals of herds not employed in forming the base. Upon detection of any new infections after administration of the vaccine, the above-described process may be repeated on a herd specific basis, adding any appearing pathogenic strains (in killed form) not previously included in the vaccine.

Accordingly, the vaccine should be altered or added too to keep pace with the changing population of pathogens in a given dairy herd, to maximize the beneficial effects. However, through the discovery of this invention, a method is provided for extended prevention over long periods of time. The periodic checks to determine preclinical mastitis must be made frequently enough to compensate for factors which may influence a change in pathogenic strains relatively quickly, such as changing weather conditions, barnyard conditions, etc.

Use of the vaccine as described above has demonstrated its effectiveness in the prevention and treatment of mastitis in bovine animals.

As noted, to therapeutically treat existing mastitis infections, the vaccine should be administered such that the concentration of killed pathogens in a pharmaceutically acceptable vehicle is on the order of $2 \times 10^{10}$ cells/milliliter of vehicle. If intramuscular injections are employed, one dose of about 15 ml should be administered daily until the infection is reversed. Alternatively, to prevent the occurrence of mastitis in uninfected cows, an intramuscular injection of a 5 ml dose should be administered weekly for a period of about 4 weeks. Thereafter, "booster" shots of 5 ml should be administered 2-3 times/yr to effectively prevent mastitis from occuring.

Of course, alternative methods of administering the vaccine other than IM injection exist. A preferred alternative is microencapsulation of the vaccine, such as through the processed addressed in U.S. Pat. Nos. 4,251,382; 4,255,411; 4,257,884 and 4,107,288. If microencapsulated, the amount administered should be adjusted to match the effective delivery of the above-described IM injection schedule.

A further alternative for administration is through controlled release, which can be achieved either through microencapsulation, or by implantation of polymeric articles containing the vaccine, through which implants the vaccine slowly migrates out or is otherwise released over time. Again, the effective dosage should match that suggested above.

Unexpectedly, the same vaccine has been demonstrated to be effective in causing reversal of hard udder syndrome. Therapeutic treatment of animals suffering from this syndrome with the vaccine according to the schedule given above for treatment of infections has caused softening of tissues previously infected, allowing resumption of pre-infection milk delivery capacities.

This invention may be further understood by reference to the Example set forth below.

EXAMPLE 1

Between the period of June, 1975 —June, 1982, milk samples from cows diagnosed as having preclinical mastitis on the San-Mar-Gale Farm in Cincinnati, Ohio were sent to the Stolle Research and Development Corporation laboratory, where the pathogenic species contained in the milk were grown in culture. These cultures are used to produce a vaccine which was used to immunize the cows. As new preclinical mastitis infections occurred, the process was repeated again and again, over a period of six years to produce a unique vaccine comprised of the combination of pathogenic species which evolved in the dairy herd.

To test the utility of the vaccine for the treatment of mastitis, cows with clinical mastitis were injected with doses of the polyvalent vaccine produced. For this experiment, 10 controlled cows were treated with conventional antibiotics, e.g., ampicillin and tetracycline. A second group of 10 cows were given no treatement. The third group of 10 cows were given 15 cc of the polyvalent vaccine daily ($2 \times 10^{10}$ per cc) until the infection was cured. The results of the experiment showed that the polyvalent vaccine was as effective as conventional antibiotics for the treatment of existing mastitis. Both the vaccine and the antibiotics were more effective than no treatment at all in controlling mastitis. The vaccine is an improvement over the antibiotics because it does not contaminate the milk, and is not likely to give rise to new, resistant pathogenic species. Moreover, treatment with the vaccine causes udders, hardened by mastitis, to soften.

Moreover, in extended treatment with both antibiotics and the vaccine, the number of mastitis infections dramatically dropped while the number of vaccine treatments increased at the expense of antibiotic treatments. These results are graphically illustrated in FIG. 1.

The vaccine and process for making that vaccine of this invention has been described above, with reference to particular and preferred embodiments. Specifically, exemplary pathogens and subject animals have been recited. However, these are advanced for illustrated purposes only, and are not intended to limit the invention. Variations will occur to those of ordinary skill in the art, particularly with respect to dosages and frequency of administration, which do not require the exercise of inventive faculty, and remain within the limits of the invention, as claimed below.

WHAT IS CLAIMED AS NEW AND DESIRED TO BE SECURED BY LETTERS PATENT OF THE UNITED STATES IS:

1. A process for the production of a polyvalent vaccine for the treatment and/or prevention of mastitis and hardened udder syndrome in bovine animals, comprising the steps of:
    (1) culturing pathogens present in the milk of a plurality of bovine animals exhibiting preclinical mastitis;
    (2) incorporating non-virulent forms of each strain of said pathogens in an appropriate pharmacological carrier in a biologically effective concentration; and
    (3) repeating said step (1) periodically and incorporating in said carrier any pathogenic strains cultured in said repeated step (1) not previously incorporated in said carrier.

2. The process of claim 1, wherein said periodic repetition occurs upon the identification of a new case of preclinical mastitis in said animals.

3. The process of claim 1, wherein said biologically effective concentration is about $2 \times 10^{10}$ pathogen cells/ml of carrier.

4. The process of claim 1, wherein said carrier is saline solution.

* * * * *

UNITED STATES PATENT AND TRADEMARK OFFICE
CERTIFICATE OF CORRECTION

PATENT NO. : 4,762,712
DATED : AUGUST 9, 1988
INVENTOR(S) : STOLLE ET AL

It is certified that error appears in the above-identified patent and that said Letters Patent is hereby corrected as shown below:

In the Abstract, at the next to last line, "demonstated" should read --demonstrated--.

Column 1, line 29, "tit" should read --teat--;
line 51, "presists" should read --persists--;
line 58, after "mastitis" insert -- , --.
Column 2, line 57, "DRAWINGS" should read --DRAWING--.
Column 3, line 66, after "herd" insert -- , --.
Column 5, line 8, "be then" should read --then be--;
line 14, "componets" should read --components--;
line 29, "non virulent" should read --non-virulent--;
line 30, "bacterial" should read --bacteria--.

UNITED STATES PATENT AND TRADEMARK OFFICE
CERTIFICATE OF CORRECTION

PATENT NO. : 4,762,712

DATED : AUGUST 9, 1988

INVENTOR(S) : STOLLE ET AL

It is certified that error appears in the above-identified patent and that said Letters Patent is hereby corrected as shown below:

Column 6, line 18, delete "too";

line 43, "occuring" should read --occurring--;

line 47, "processed" should read --processes--.

Signed and Sealed this

Seventh Day of March, 1989

Attest:

DONALD J. QUIGG

*Attesting Officer*  *Commissioner of Patents and Trademarks*